US008715761B2

(12) United States Patent
Daniher et al.

(10) Patent No.: US 8,715,761 B2
(45) Date of Patent: *May 6, 2014

(54) FLAVOR MOLECULES

(75) Inventors: Andrew Daniher, Cincinnati, OH (US); Yili Wang, Mason, OH (US)

(73) Assignee: Givaudan S.A., Vernier (CH)

( * ) Notice: Subject to any disclaimer, the term of this patent is extended or adjusted under 35 U.S.C. 154(b) by 620 days.

This patent is subject to a terminal disclaimer.

(21) Appl. No.: 12/795,201

(22) Filed: Jun. 7, 2010

(65) Prior Publication Data

US 2010/0272656 A1  Oct. 28, 2010

Related U.S. Application Data

(63) Continuation-in-part of application No. 12/389,900, filed on Feb. 20, 2009.

(60) Provisional application No. 61/031,146, filed on Feb. 25, 2008.

(51) Int. Cl.
*A23L 1/236* (2006.01)
*A23L 1/229* (2006.01)
*C07D 213/59* (2006.01)
*C07D 213/80* (2006.01)
*C07D 401/04* (2006.01)
*C07D 213/38* (2006.01)
*C07D 213/64* (2006.01)
*C07D 213/67* (2006.01)
*C07D 277/30* (2006.01)
*C07D 277/24* (2006.01)

(52) U.S. Cl.
USPC ........ 426/548; 426/537; 544/131; 546/276.4; 546/301; 548/204

(58) Field of Classification Search
USPC ........ 426/537, 548; 544/131; 546/276.4, 301; 548/204
See application file for complete search history.

(56) References Cited

U.S. PATENT DOCUMENTS

| | | | |
|---|---|---|---|
| 3,956,375 A | 5/1976 | Farkas et al. | |
| 3,976,790 A | 8/1976 | Crosby et al. | |
| 4,626,442 A | 12/1986 | Zanno et al. | |
| 5,731,292 A | 3/1998 | Tsujihara et al. | |

FOREIGN PATENT DOCUMENTS

| FR | 2 164 676 A | 8/1973 |
|---|---|---|
| WO | WO 2007/107596 A1 | 9/2007 |

OTHER PUBLICATIONS

PCT/CH2009/000075 International Search Report, Jun. 12, 2009.
Whitelaw and Daniel, Synthesis and Sensory Evaluation of Ring-Substituted Dihydrochalcone Sweeteners, Journal of Agriculture and Food Chemistry, 1991, 44-51, vol. 39 No. 1, American Chemical Society, Washington, D.C.
Whitelaw, Chung, and Daniel, Synthesis and Sensory Evaluation of Ring-Substituted Dihydrochalcone Sweeteners. 2 Analogues of 3'-Carboxyhesperetin Dihydrochalcone, a High-Potency Dihydrochalcone Sweetener. Journal of Agriculture and Food Chemistry. 1991, 663-667 vol. 39 No. 4. American Chemical Society, Washington, D.C.
Yamato, M. et al., "Chemical structure and sweet taste of isocoumarines and related conpounds. X. Syntheses of sweet 5-hydroxyflavones and related dihydrochalcones". Chemical and Pharmaceutical Bulletin, vol. 26, No. 8, Jan. 1, 1978. pp. 2321-2327, XP002489895.
International Preliminary Report on Patentability, Form PCT/IB/373 for PCT International Patent Application No. PCT/CH2009/000075, mailing date Aug. 31, 2010.
United States Patent and Trademark Office Office Action, mailed Mar. 8, 2012, U.S. Appl. No. 12/389,900, filed Feb. 20, 2009.
Yasar, Ahmet, et al.; "Microwave-Assisted Synthesis of 4'-Azaflavones and Their N-Alkyl Derivatives with Biological Activities"; Chemistry & Biodiversity; 2008; pp. 830-838; vol. 5; Verlag Helvetica Chimica Acta AG, Zurich.
CAS/STN Search History, Jan. 26, 2012, U.S. Appl. No. 12/389,900.

*Primary Examiner* — D. Lawrence Tarazano
*Assistant Examiner* — Juliya Kravets
(74) *Attorney, Agent, or Firm* — Curatolo Sidoti Co., LPA; Joseph G. Curatolo; Salvatore A. Sidoti

(57) ABSTRACT

A method of providing a range of flavors to an orally-receivable or ingestible product, the method including adding at least one compound, including salts thereof, of the formula:

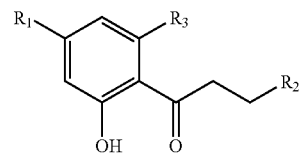

wherein $R_1$ may be H, OH, $O(CH_2)_2OH$, $OCH_2OCH_3$ or

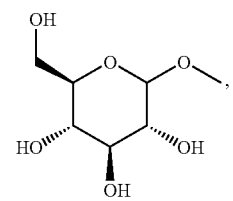

$R_2$ may be selected from a range of 5- and 6-membered heterocyclic rings, and wherein $R_3$ may be H or OH. The compounds give rise to a wide range of flavors, and some are useful as sweetness enhancers, this allowing sweetener content to be reduced while maintaining sweetness. Also disclosed are orally-receivable or ingestible products including the compounds.

24 Claims, No Drawings

FLAVOR MOLECULES

This application is a continuation-in-part of co-pending U.S. Ser. No. 12/389,900, filed Feb. 20, 2009, which claims the benefit of the filing date, under 35 U.S.C. §119(e), of U.S. Provisional Application for Patent Ser. No. 61/031,146, filed Feb. 25, 2008, which applications are incorporated herein by reference.

This disclosure relates to flavours, compounds for providing flavours and methods for providing flavours.

Flavoring is added to many orally-receivable or ingestible products, such as foodstuffs, confectionery, beverages, mouthwashes, dentrifices and the like. It is preferred that these be identical to natural materials known to be safe, or to be close derivatives of such materials.

Flavonoids are usually regarded as bitter or neutral-lasting plant constituents. However, there are flavonoids in two structural classes, which are known as sweet representative: the dihydrochalcones (DHCs) and the dihydroflavonols. Only a few dihydrochalcones have been identified from natural sources. Glycyphylin, Phloridzin and trilobatin are the examples isolated from *Smilax glycyphylla* Sm. (Liliaceae), *Symplocos lancifolia* Sieb. Et Zucc., and *Symplocus microcaly*, respectively. Normally, DHCs, molecules with a basic structure according to the following formula

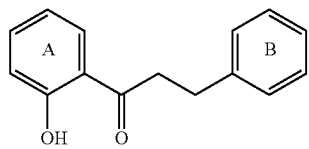

are derived from bitter flavanone glycosides in citrus fruits by catalytic reduction of the chalcones. The best-known semi-synthetic DHC is neohesperidine dihydrochalcone (NDHC), which can be obtained as a by-product of citrus industry and is used in a wide variety of foodstuffs as a sweetener and flavor ingredient.

In the past 20 years there have been many attempts to produce dihydrochalcone analogs with taste qualities as good as that of sucrose. It was concluded from these studies that highly sweet compounds in this series required a 3-hydroxy-4-alkoxy substitution in ring B (Whitelaw and Daniel; Journal of Agricultural and Food Chemistry (1991), 39(4), pp. 663-7; and Journal of Agricultural and Food Chemistry (1991), 39(1), pp. 44-51).

It has now been found that a range of DHC-based compounds are capable of conferring a wide variety of flavors and flavor modifications. There is therefore provided a method of providing flavor to a composition adapted to be received orally, comprising adding thereto at least one compound of the formula:

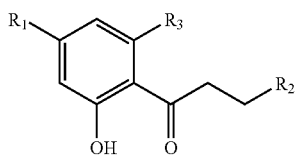

or a salt thereof, wherein $R_1$ comprises H, OH, $O(CH_2)_2OH$, $OCH_2OCH_3$ or

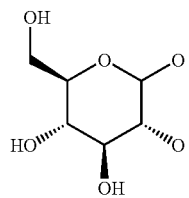 [SMILES: OC[C@H]1OC(O)[C@H](O)[C@@H](O)[C@@H]1O]

wherein $R_2$ comprises a heterocyclic moiety selected from

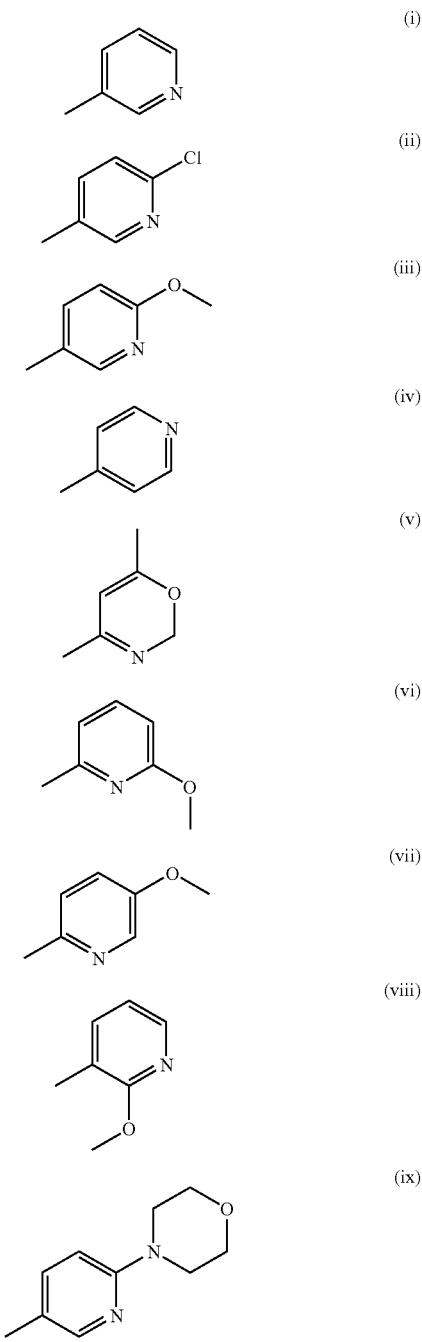

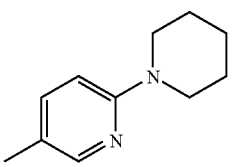 (x)

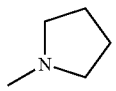 (xi)

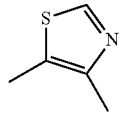 (xii)

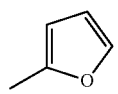 (xiii)

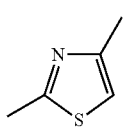 (xiv)

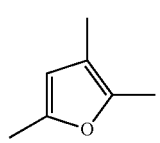 (xv)

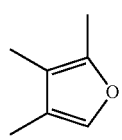 (xvi)

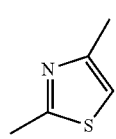 (xvii)

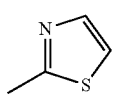 (xviii)

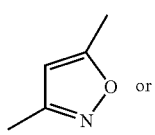 or (xix)

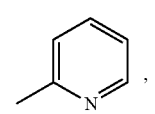, (xx)

and wherein $R_3$ comprises H or OH.

Suitable non-limiting examples of salts of the above identified compounds include $K^+$, $NH_4^+$, $Na^+$, $Ca^{2+}$, $Mg^{2+}$, $Al^{3+}$, $Zn^{2+}$, hydrochloride and hydrobromide.

Certain illustrative embodiments comprise compounds comprising moieties (iii), (iv), (vii), (viii), (xiii), (xvii), or (xviii). In a particular embodiment, $R^1$ is H, $R^3$ is H, and $R^2$ is moiety (iv) in the form of its hydrochloride or hydrobromide salt.

The compounds confer a wide variety of desirable flavors, such as sweet, sour and umami, to orally receivable or digestable products. Specific examples of these flavor characteristics are described in further detail in the examples hereinunder provided.

A number of the molecules hereinabove provided are novel materials. Some of the compounds hereinabove described are novel. There is therefore additionally provided a compound of the formula:

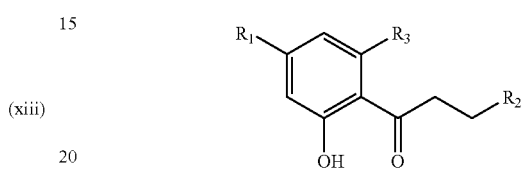

or a salt thereof,
wherein $R_1$ comprises H, OH, $O(CH_2)_2OH$, $OCH_2OCH_3$ or

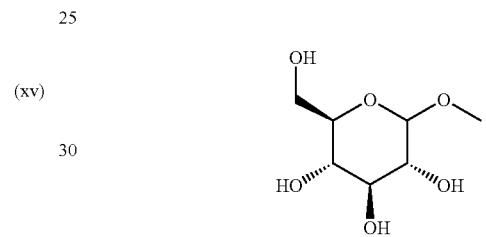

wherein $R_3$ comprises H or OH,
with the proviso that
(a) when $R^1$ comprises H, $R^2$ comprises a moiety selected from (iii), (iv), (vi), (viii), (x), (xii), (xiii), (xiv), (xvi), (xvii), (xviii), (xix), or (xx);
(b) when $R^1$ comprises OH, $R^2$ comprises moiety (iii) or (iv);
(c) when $R^1$ comprises —$OCH_2OCH_3$, $R_2$ comprises moiety (iii) or (iv);
(d) when $R^1$ comprises

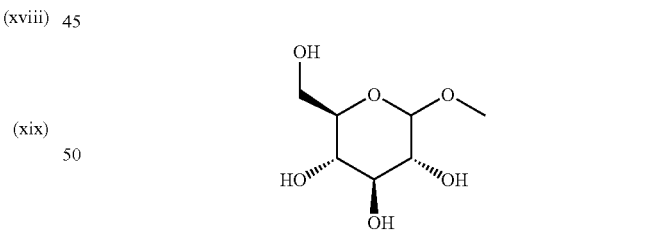

$R^2$ comprises moiety (iii) or (iv); and
(e) when $R^1$ comprises —$OCH_2CH_2OH$, $R^2$ comprises moiety (iii).

The compounds, or a salt thereof, may be used in all variety of orally-receivable and ingestible products, including but not limited to sweetener-containing consumable products.

Non-limiting examples of such products include:
Consumable products, including, but not limited to all food products, food additives, nutraceuticals, pharmaceuticals and any product placed in the mouth including chewing gum, oral care products, and oral hygiene products including but not limited to, cereal products, rice products, tapioca products, sago products, baker's products, biscuit products, pastry products, bread products, confectionery products, dessert products, gums, chewing gums, flavored or flavor-coated straws, flavor or flavor-coated food/beverage containers, chocolates, ices, honey products, treacle products, yeast products, baking-powder, salt and spice products, savoury products, mustard products, vinegar products, sauces (condiments), tobacco products, cigars, cigarettes, processed foods, cooked fruits and vegetable products, meat and meat products, jellies, jams, fruit sauces, egg products, milk and dairy products, yoghurts, cheese products, butter and butter substitute products, milk substitute products, soy products, edible oils and fat products, medicaments, beverages, carbonated beverages, alcoholic drinks such as beers, wines and spirits, non-alcoholic drinks such as soft drinks, mineral and aerated waters, fruit drinks, fruit juices, coffee, artificial coffee, tea, cocoa, including forms requiring reconstitution including, without limitation, beverage powder, milk based beverage powder, sugar-free beverage powder, beverage syrup, beverage concentrate, instant coffee, instant tea, instant cocoa, and coffee whitener, food extracts, plant extracts, meal extracts, condiments, gelatins, pharmaceutical and non-pharmaceutical gums, tablets, lozenges, drops, emulsions, elixirs, syrups and other preparations for making beverages, and combinations thereof.

Oral care products, including, but not limited to, any composition applied to the oral cavity for the purposes of cleaning, freshening, healing, deodorising the cavity or any part thereof, may include, but are not limited to, toothpastes, tooth gels, tooth powders, tooth whitening products, mouthwashes, lozenges, dental floss, toothpicks, anti-plaque and anti-gingivitis compositions, throat lozenges, throat drops, inflammatory compositions, compositions for treatment of nasal symptoms, cold symptoms and upper gastrointestinal tract distress, compositions for cold relief, for alleviating discomfort of hot flash, and gargle compositions.

The proportion of compound used will vary in every case, depending upon the end use and the nature and extent of taste required. This may be readily determined in every case by one having ordinary skill in the art by routine experimentation. Without limitation, and by way of illustration only, proportions of compound may be in the range of about 0.01 to about 600 ppm depending on the application. Typical, non-limiting examples in a beverage are from about 1 to about 50 ppm, in ice cream from about 10 to about 100 ppm, and in cereal from about 10 top about 150 ppm.

According to certain illustrative embodiments, the compounds may be used in such products with known flavor compounds, and also with all the known ancillary compounds used in flavoured products.

According to one illustrative aspect of the disclosure, it has been found that one of these compounds enhances the sweetness of a sugar-containing product in a synergistic fashion, that is, the overall sweetness is higher than the simple sum of the sweetness of two sweet substances. This compound has little sweet taste of its own, but it causes a considerable increase in the perceived sweetness of a sugar-containing product. This is of great interest, given the current interest in improved diet and the desire to decrease the sugar content of consumable products sweetness for dietary or health reasons.

According to other embodiments, also provided is a method of decreasing the sugar content of a sugar-containing consumable product, comprising adding to said sugar-containing consumable product an effective amount of 1-(2-hydroxyphenyl)-3-(pyridin-4-yl)propan-1-one (hereinafter referred to as "Compound 13", the number of the Example below in which it is described) or a hydrochloride or hydrobromide salt thereof.

The sweet enhancement effect of Compound 13 is illustrated in the following tables: the isointensity of Compound 13 at 20 ppm equals 0.5% sucrose. The isointensity of 7% sucrose with 20 ppm 1-(2-hydroxyphenyl)-3-(pyridin-4-yl)propan-1-one is 8% sucrose. Therefore, the perceived enhancement of sucrose is about 0.5% sucrose (8%-7.5%). This sweet enhancement effect is also observed with consumable products containing other natural and artificial sweeteners, for example, carbohydrates; sucrose, lactose, D-glucose, D-tagatose, D-fructose whether naturally- or synthetically-produced, erythritol, threitol, arabitol, ribitol, xylitol, sorbitol, mannitol, maltitol, isomaltitol, dulcitol, and lactitol, thaumatin, glycin, D-phenylalanine, D-tryptophan, sodium cyclamate, acesulfam K, neohesperidine dihydrochalcone, sodium salt of saccharin, aspartame, superaspartame, neotam, alitam, sucralose, and stevioside.

| Isointensity of 20 ppm Compound 13 in water. | | | | |
|---|---|---|---|---|
| solutions compared | sample sweetness | R-index [%] | Critical value [%] | p-value |
| 0.5% sucrose vs. 20 ppm Compound 13 | isosweet | 61% | 64.61 | P > 0.05 |
| 1% sucrose vs. 20 ppm Compound 13 | less sweet | 14% | 35.39 | P < 0.05 |

| Isointensity of 7% sucrose + 20 ppm Compound 13 in water. | | | | |
|---|---|---|---|---|
| solutions compared | sample sweetnes | R-index | Critical value | p-value |
| 7% sucrose vs. 7% sucrose + 20 ppm Cmpd 13 | sweeter | 66% | 64.61 | P < 0.05 |
| 8% sucrose vs. 7% sucrose + 20 ppm Cmpd 13 | isosweet | 43% | 35.39 | P > 0.05 |
| 9% sucrose vs. 7% sucrose + 20 ppm Cmpd 13 | less sweet | 8% | 35.39 | P < 0.05 |
| 10% sucrose vs. 7% sucrose + 20 ppm Cmpd 13 | less sweet | 4% | 35.39 | P < 0.05 |

By "effective amount" is meant the amount needed to produce the desired level of sweetness, while reducing the level of sugar to the desired extent. This will naturally depend on the nature of the product and how much sweetness is desired, so no rigid limits can or should be set, but in every case a suitable level my be determined by one having ordinary skill in the art by routine experimentation. Without limitation, and by way of illustration only, proportions may be in the range of about 0.1 to about 500 ppm.

Compound 13 may be used in conjunction with any known flavour molecule, sweetener, and sweetness enhancer such as naringen dihydro chalcone.

The disclosure is now further illustrated by the following examples, which are purely exemplary and which are not intended to be in any manner limiting on the scope of the disclosure.

EXAMPLE 1

1-(2-hydroxyphenyl)-3-(6-methoxypyridin-3-yl) propan-1-one

To a stirring solution of 2-hydroxyacetophenone (2.19 g, 16.1 mmol) in EtOH (30 ml) at room temperature was added 6-methoxy-3-pyridine-carboxaldehyde (1.98 g, 14.4 mmol)

and 10 ml solution of KOH in water (1.8 g, 32.1 mmol). The solution was continuously stirred at room temperature for 5 hours, and then water was added to the reaction flask. The aqueous layer was acidified to pH=7 using 1N HCl and extracted three times with EtAOc. The organic layers combined and dried ($Na_2SO_4$). The solvent was removed in vacuo and the residue chromatographed on silica gel (5% EtOAc/Hex) to give the yellow solid which was recrystallized with hot EtOAc/hex to yield 1.2 g of product (32%). $^1$H NMR (300 MHz, $CDCl_3$): δ 12.83 (s, 1H), 8.43 (d, J=2.4 Hz, 1H), 7.96-7.89 (m, 2H), 7.91 (d, J=15.3 Hz, 1H), 7.57 (d, J=15.6 Hz, 1H), 7.52 (d, d, J=6.9, 7.2 Hz, 1H), 7.05 (d, J=8.4 Hz, 1H), 6.97 (d, d, J=6.9, 7.5 Hz, 1H), 6.84 (d, J=8.7 Hz, 1H), 4.01 (s, 3H).

$^{13}$C NMR (75.5 Hz, $CDCl_3$) δ 193.28, 165.72, 163.64, 149.47, 141.94, 136.61, 136.39, 129.50, 124.04, 119.94, 118.88, 118.84, 118.69, 111.74, 53.92.

HPLCMS (APCI+): m/z=256.2.

In a 100 ml round-bottom flask, 0.53 g of chalcone (2.08 mmol) and 90 mg of 10% Pd/C (0.86 mmol) was mixed together in 20:10 ml THF:MeOH solution. Hydrogenation at atmospheric pressure then filtered off the catalyst. The crude was purified by chromatography on silica gel (10% EtOAc/hexane) to provide 0.35 g (58%) of final compound. $^1$H NMR (300 MHz, $CDCl_3$): δ 12.15 (s, 1H), 7.97 (d, J=2.4 Hz, 1H), 7.65 (d, d, J=1.5, 8.1 Hz, 1H), 7.41-7.36 (m, 2H), 6.91 (d, d, J=0.9, 8.4 Hz, 1H), 6.80 (d, d, d, J=1.2, 7.5, 8.4 Hz, 1H), 6.62 (d, J=8.7 Hz, 1H), 3.84 (s, 3H), 3.21 (t, J=7.5 Hz, 2H), 2.92 (t, J=7.5 Hz, 2H).

$^{13}$C NMR (75.5 Hz, $CDCl_3$) δ 204.86, 163.00, 162.50, 146.22, 138.95, 136.43, 129.69, 128.63, 119.24, 118.95, 118.63, 110.67, 53.33, 39.74, 26.18.

HPLCMS (APCI+): m/z=258.1.

EXAMPLE 2

1-(2-hydroxyphenyl)-3-(6-methoxypyridin-2-yl) propan-1-one 2.35 g (17.3 mmol) of 2-hydroxyacetophenone, 2.13 g of 6-methoxy-2-pyridinecarboxaldehyde (15.5 mmol), and 8 ml of 25% $NaOCH_3$ were reacted in 70 ml dry THF to give 1.2 g (30%) of chalcone after purification. $^1$H NMR (300 MHz, $CDCl_3$): δ 12.15 (s, 1H), 8.24 (d, J=14.7 Hz, 1H), 8.01 (d, d, J=1.2, 7.8 Hz, 1H), 7.79 (d, J=15.0 Hz, 1H), 7.65 (d, d, J=7.2, 7.2 Hz, 1H), 7.53 (d, d, J=7.2, 7.2 Hz, 1H), 7.10 (d, J=7.2 Hz, 1H), 7.06 (d, d, J=0.9, 8.1 Hz, 1H), 6.99 (d, J=7.2, 8.1 Hz, 1H), 6.83 (d, J=8.4 Hz, 1H), 4.08 (s, 3H).

$^{13}$C NMR (75.5 Hz, $CDCl_3$) δ 194.32, 163.81, 163.66, 150.24, 143.26, 139.15, 136.52, 130.03, 123.57, 120.18, 119.71, 118.88, 118.58, 113.32, 53.33.

HPLCMS (APCI+): m/z=256.0.

Hydrogenation of 1.52 g of chalcone with catalytic amount of 10% Pd/C obtained 1.25 g (82%) of dihydrochalcone after purification on silica gel chromatography (5% EtOAc/hexane). $^1$H NMR (300 MHz, $CDCl_3$): δ 12.39 (s, 1H), 7.83 (d, d, J=1.5, 7.8 Hz, 1H), 7.46-7.41 (m, 2H), 6.96 (d, d, J=0.9, 8.4 Hz, 1H), 6.86 (d, d, J=6.9, 7.5 Hz, 1H), 6.77 (d, J=7.2 Hz, 1H), 6.54 (d, J=8.1 Hz, 1H), 3.77 (s, 3H), 3.46 (t, J=7.2 Hz, 2H), 3.17 (t, J=7.2 Hz, 2H).

$^{13}$C NMR (75.5 Hz, $CDCl_3$) δ 205.86, 163.71, 162.43, 157.65, 138.79, 136.11, 129.99, 119.54, 118.83, 118.37, 115.34, 107.96, 52.95, 36.57, 31.39.

HPLCMS (APCI+): m/z=258.1.

EXAMPLE 3

1-(2-hydroxyphenyl)-3-(2-methoxypyridin-3-yl) propan-1-one 2.39 g (17.6 mmol) of 2-hydroxyacetophenone, 2.10 g of 2-methoxy-3-pyridinecarboxaldehyde (15.3 mmol), and 10 ml of 25% $NaOCH_3$ were reacted in 50 ml of dry THF to give 2.35 g (60%) of chalcone after purification. $^1$H NMR (300 MHz, $CDCl_3$): δ 12.85 (s, 1H), 8.24 (d, d, J=1.8, 4.8 Hz, 1H), 8.02 (d, J=15.6 Hz, 1H), 7.94-7.86 (m, 2H), 7.90 (d, J=15.9 Hz, 1H), 7.52 (d, d, J=8.4, 8.7 Hz, 1H), 7.06-6.98 (m, 3H), 4.12 (s, 3H).

$^{13}$C NMR (75.5 Hz, $CDCl_3$) δ 194.06, 163.65, 162.40, 148.70, 139.84, 138.91, 136.36, 129.72, 122.69, 120.08, 118.83, 118.62, 118.23, 117.17, 53.88. HPLCMS (APCI+): m/z=256.0.

Hydrogenation of 0.45 g of chalcone with catalytic amount of 10% Pd/C obtained 0.39 g (87%) of dihydrochalcone after purification on silica gel chromatography (5% EtOAc/hexane). $^1$H NMR (300 MHz, $CDCl_3$): δ 12.31 (s, 1H), 8.07 (d, d, J=2.1, 5.1 Hz, 1H), 7.78 (d, d, J=1.8, 8.1 Hz, 1H), 7.50-7.45 (m, 2H), 6.99 (d, d, J=0.9, 8.1 Hz, 1H), 6.89 (d, d, J=7.2, 8.1 Hz, 1H), 6.85 (d, d, J=5.1, 5.6 Hz, 1H), 3.98 (s, 3H), 3.32 (t, J=7.8 Hz, 2H), 3.02 (t J=7.8 Hz, 2H).

$^{13}$C NMR (75.5 Hz, $CDCl_3$) δ 205.66, 162.47, 162.11, 144.87, 138.32, 136.28, 129.89, 123.11, 119.34, 118.87, 118.52, 116.82, 53.32, 37.57, 25.23.

HPLCMS (APCI+): m/z=258.1.

EXAMPLE 4

1-(2-hydroxyphenyl)-3-(4-methylthiazol-5-yl)propan-1-one 2.21 g (16.3 mmol) of 2-hydroxyacetophenone, 1.96 g of 4-methylthiazole-5-carboxaldehyde (7.86 mmol), and 10 ml of 25% $NaOCH_3$ were reacted in 50 ml of dry THF to give 1.59 g (5.2%) of chalcone after purification. $^1$H NMR (300 MHz, $CDCl_3$): δ 12.73 (s, 1H), 8.76 (s, 1H), 8.05 (d, d, J=0.9, 15.0 Hz, 1H), 7.82 (d, d, J=1.5, 8.1 Hz, 1H), 7.49 (d, d, d, J=1.5, 7.2, 8.4 Hz, 1H), 7.31 (d, J=15.0 Hz, 1H), 7.00 (d, d, J=0.9, 8.4 Hz, 1H), 6.95-6.93 (m, 1H), 2.62 (s, 3H).

$^{13}$C NMR (75.5 Hz, $CDCl_3$) δ 192.60, 163.62, 157.68, 153.29, 136.66, 134.28, 132.96, 129.46, 129.03, 121.63, 119.71, 119.26, 118.93, 118.66, 15.82.

HPLCMS (APCI+): m/z=246.1

Hydrogenation of 0.48 g (1.96 mmol) of chalcone with catalytic amount of 10% Pd/C obtained 0.15 g (27%) of dihydrochalcone after purification on silica gel chromatography (25% EtOAc/hexane). $^1$H NMR (300 MHz, $CD_3OD$): δ 8.73 (s, 1H), 7.87 (d, d, J=1.8, 8.4 Hz, 1H), 7.49 (d, d, d, J=1.5, 7.2, 8.1 Hz, 1H), 6.97-6.91 (m: 2H), 3.42 (t, J=6.9 Hz, 2H), 3.25 (t, J=6.9 Hz, 2H), 2.41 (s, 3H).

$^{13}$C NMR (75.5 Hz, $CD_3OD$) δ 206.17, 163.24, 151.88, 149.84, 137.49, 132.31, 131.43, 120.82, 120.27, 119.05, 40.66, 21.40, 14.57. HPLCMS (APCI+): m/z=248.0

EXAMPLE 5

1-(2-hydroxyphenyl)-3-(6-(pyrrolidin-1-yl)pyridin-3-yl)propan-1-one 1.85 g (13.6 mmol) of 2-hydroxyacetophenone, 2.0 g of 6-(pyrrolidin-1-yl)nicotinaldehyde (1.34 mmol), and 10 ml of 25% $NaOCH_3$ were reacted in 50 ml of dry THF to give 2.2 g (65%) of chalcone after purification. $^1$H NMR (300 MHz, CDCl$_3$): δ 13.13 (bs, 1H), 8.34 (d, J=2.4 Hz, 1H), 7.85 (d, J=15.3 Hz, 1H), 7.84 (d, J=1.5 Hz, 1H), 7.74 (d, d, J=2.4, 9.0 Hz, 1H), 7.43 (d, d, d, J=1.5, 7.2, 8.4 Hz, 1H), 7.37 (d, J=15.3 Hz, 1H), 6.98 (d, d, J=0.9, 8.4 Hz, 1H), 6.89 (d, d, d, J=0.9, 7.2, 8.1 Hz, 1H), 6.37 (d, J=9.0 Hz, 1H), 3.49 (bs, 4H), 2.05-1.96 (m, 4H).

$^{13}$C NMR (75.5 Hz, CDCl$_3$) δ 193.18, 163.52, 157.88, 152.24, 143.78, 135.76, 135.03, 129.32, 120.21, 118.62, 118.46, 118.37, 114.49, 107.04, 46.97, 25.38.

HPLCMS (API-ES): m/z=295.1.

Hydrogenation of 0.65 g (2.21 mmol) of chalcone with catalytic amount of 10% Pd/C obtained 0.46 g (70%) of dihydrochalcone after purification on silica gel chromatography (5% EtOAc/hexane). $^1$H NMR (300 MHz, CD$_3$OD): δ 7.89-7.85 (m, 2H), 7.50-7.43 (m, 2H), 6.94-6.89 (m, 2H), 6.43 (d, J=8.7 Hz, 1H); 3.39-3.29 (m, 6H), 2.90 (t, J=7.2 Hz, 2H), 2.02-1.98 (m, 4H).

$^{13}$C NMR (75.5 Hz, CD$_3$OD) δ 205.95, 161.92, 155.96, 146.25, 137.93, 135.92, 130.13, 123.17, 119.41, 118.77, 117.62, 106.91, 46.45, 39.55, 26.03, 25.02.

HPLCMS (API-ES): m/z=297.2.

EXAMPLE 6

1-(2-hydroxyphenyl)-3-(5-methylisoxazol-3-yl)propan-1-one 2.24 g (16.5 mmol) of 2-hydroxyacetophenone, 1.65 g of 5-methylisoxazole-3-carbaldehyde (14.9 mmol), and 10 ml of 25% NaOCH$_3$ were reacted in 50 ml of dry THF to give 1.59 g (29%) of chalcone after purification. $^1$H NMR (300 MHz, CDCl$_3$): δ 12.53 (s, 1H), 7.87 (d, d. J=0.6, 7.5 Hz, 1H), 7.80 (d, J=15.6 Hz, 1H), 7.69 (d, J=15.6 Hz, 1H), 7.56-7.51 (m, 1H), 7.05 (d, d, J=0.6, 8.4 Hz, 1H), 6.99-6.93 (m, 1H), 6.31 (d, J=0.3 Hz, 1H), 2.50 (s, 3H).

$^{13}$C NMR (75.5 Hz, CDCl$_3$) δ 193.08, 170.59, 163.68, 159.84, 136.96, 132.03, 129.81, 126.62, 119.62, 119.02, 118.73, 99.99, 12.32. HPLCMS (APCI+): m/z=230.1.

Hydrogenation of 0.61 g (2.66 mmol) of chalcone with catalytic amount of 10% Pd/C obtained 0.69 g (68%) of dihydrochalcone after purification on silica gel chromatography (10% EtOAc/hexane). $^1$H NMR (300 MHz, CD$_3$OD): δ 7.92 (d, d. J=1.5, 8.4 Hz, 1H), 7.51 (d, d, d, J=1.5, 7.2, 8.4 Hz, 1H), 6.98-6.93 (m, 2H), 6.95 (bs, 1H), 3.49 (t, J=7.2 Hz, 2H), 3.05 (t, J=7.2 Hz, 2H), 2.39 (bs, 3H).

$^{13}$C NMR (75.5 Hz, CD$_3$OD) δ 206.08, 171.14, 164.76, 163.23, 137.42, 131.41, 120.75, 120.26, 119.04, 102.77, 37.30, 21.21, 11.92.

HPLCMS (API-ES): m/z=232.1.

EXAMPLE 7

1-(2-hydroxyphenyl)-3-(pyridin-3-yl)propan-1-one 2.36 g (17.3 mmol) of 2-hydroxyacetophenone, 1.7 g of 3-pyridine-carboxaldehyde (15.9 mmol), and 9 ml of 25% wt NaOCH$_3$ were reacted in 50 ml of dry THF to give 2.05 g (57%) of chalcone after purification. $^1$H NMR (300 MHz, CDCl$_3$): δ 12.66 (s, 1H), 8.93 (d, J=1.8 Hz, 1H), 8.67 (d, d, J=1.5, 4.8 Hz, 1H), 8.03-8.00 (m, 1H), 7.92 (d, J=15.7 Hz, 1H), 7.91 (d, J=1.5 Hz, 1H), 7.76 (d, J=15.6 Hz, 1H), 7.58-7.52 (m, 1H), 7.43 (d, d, J=5.1, 8.1 Hz, 1H), 7.07 (d, d, J=0.9, 8.1 Hz, 1H), 6.99 (d, d, d, J=1.2, 7.2, 8.1 Hz, 1H).

$^{13}$C NMR (75.5 Hz, CDCl$_3$) δ 193.11, 163.70, 151.26, 149.97, 141.47, 136.75, 134.87, 130.49, 129.64, 123.86, 122.22, 119.81, 119.00, 118.77.

HPLCMS (APCI+): m/z=226.1.

Hydrogenation of 0.62 g (2.76 mmol) of chalcone with catalytic amount of 10% Pd/C obtained 0.31 g (50%) of dihydrochalcone after purification on silica gel chromatography (10% EtOAc/hexane). $^1$H NMR (300 MHz, CD$_3$OD): δ 8.51 (d, J=1.8 Hz, 1H), 8.37 (d, d, J=1.5, 4.8 Hz, 1H), 7.91 (d, d, J=1.8, 8.4 Hz, 1H), 7.81 (d, d, J=1.8, 7.8 Hz, 1H), 7.49 (m, 1H), 7.37 (d, d, J=5.1, 8.1 Hz, 1H), 6.97-6.91 (m, 2H), 3.49 (t, J=7.2 Hz, 2H), 3.11 (t, J=7.2 Hz, 2H).

$^{13}$C NMR (75.5 Hz, CD$_3$OD) δ 206.61, 163.27, 150.33, 147.81, 138.92, 138.43, 137.41, 131.49, 125.14, 120.80, 120.24, 119.04, 40.28, 27.94.

HPLCMS (API-ES): m/z=228.1.

EXAMPLE 8

3-(furan-2-yl)-1-(2-hydroxyphenyl)propan-1-one 2.27 g (16.7 mmol) of 2-hydroxyacetophenone, 1.52 g of furan-2-carbaldehyde (15.8 mmol), and 10 ml of 25% wt NaOCH$_3$ were reacted in 50 ml of dry THF to give 2.4 g (71%) of chalcone after purification. $^1$H NMR (300 MHz, CDCl$_3$): δ 12.90 (s, 1H), 7.94 (d, d, J=1.5, 8.1 Hz, 1H), 7.71 (d, J=15.0 Hz, 1H), 7.58 (d, J=15.0 Hz, 1H), 7.58 (d. J=1.5 Hz, 1H), 7.51 (d, d, d, J=1.5, 7.2, 8.4 Hz, 1H), 7.04 (d, d, J=0.9, 8.4 Hz, 1H), 6.96 (d, d, J=8.1, 8.1 Hz, 1H), 6.79 (d, J=3.3 Hz, 1H), 6.56 (d, d, J=1.5, 3.3 Hz, 1H).

$^{13}$C NMR (75.5 Hz, CDCl$_3$) δ 193.31, 163.57, 151.56, 145.41, 136.27, 131.11, 129.63, 120.08, 118.83, 118.54, 117.67, 117.06, 112.88.

HPLCMS (APCI+): m/z=215.1.

Hydrogenation of 0.48 g (2.24 mmol) of chalcone with catalytic amount of 10% Pd/C obtained 0.26 g (54%) of dihydrochalcone after purification on silica gel chromatography (5% EtOAc/hexane). $^1$H NMR (300 MHz, CDCl$_3$): 12.25 (s, 1H), 7.79 (d, d, J=1.5, 8.1 Hz, 1H), 7.48 (d, d, d, J=1.5, 7.2, 8.4 Hz, 1H), 7.34-7.28 (m, 1H), 7.01 (d, d, J=0.9, 8.4 Hz, 1H), 6.92 (d, d, d, J=1.2, 7.5, 8.4 Hz, 1H), 6.32-6.30 (m, 1H), 6.09-6.08 (m, 1H), 3.39 (t, J=7.2 Hz, 2H), 3.12 (t, J=7.5 Hz, 2H).

$^{13}$C NMR (75.5 Hz, CDCl$_3$) δ 204.75, 162.44, 154.27, 141.26, 136.37, 129.83, 119.28, 118.96, 118.53, 110.36, 105.58, 36.56, 22.55.

HPLCMS (API-ES): m/z=216.9.

EXAMPLE 9

1-(2-hydroxyphenyl)-3-(6-morpholinopyridin-3-yl)propan-1-one 2.5 g (15.8 mmol) of 2-hydroxyacetophenone, 2.8 g of 4-morpholinobenzaldehyde (14.5 mmol), and 10 ml of 25% wt NaOCH$_3$ were reacted in 50 ml of dry THF to give 2.52 g (56%) of chalcone after purification. $^1$H NMR (300 MHz, CDCl$_3$): δ 12.99 (s, 1H), 8.43 (d, J=2.4 Hz, 1H), 7.93-7.84 (m, 3H), 7.52-7.48 (m, 2H), 7.03 (d, d, J=0.9, 8.4 Hz, 1H), 6.97-6.92 (m, 1H), 6.68 (d, J=9.0 Hz, 1H), 3.86-3.83 (m, 4H), 3.69-3.66 (m, 4H).

$^{13}$C NMR (75.5 Hz, CDCl$_3$) δ 193.27, 163.58, 159.87, 151.09, 142.84, 136.03, 135.90, 129.38, 120.18, 120.13, 118.70, 118.59, 116.27, 106.44, 66.58, 45.09.

HPLCMS (APCI+): m/z=311.2.

Hydrogenation of 0.341 g (1.10 mmol) of chalcone with catalytic amount of 10% Pd/C obtained 0.44 g of dihydrochalcone after purification on silica gel chromatography (10% EtOAc/hexane). $^1$H NMR (300 MHz, CD$_3$OD): δ 8.04 (d, J=1.8 Hz, 1H), 7.90 (d, d, J=1.5, 8.1 Hz, 1H), 7.55 (d, d, J=2.7, 8.7 Hz, 1H), 7.52-7.46 (m, 1H), 6.96-6.88 (m, 2H), 6.79 (d, J=7.2 Hz, 1H) 3.81-3.78 (m, 4H), 3.43-3.35 (m, 6H), 2.97 (t, J=7.2 Hz, 2H).

$^{13}$C NMR (75.5 Hz, CD$_3$OD) δ 205.19, 160.51, 157.95, 146.96, 137.79, 135.95, 130.68, 125.65, 120.35, 119.17, 117.60, 106.86, 65.93, 45.42, 25.68, 0.07.

HPLCMS (API-ES): m/z=313.0.

EXAMPLE 10

3-(4,5-dimethylfuran-2-yl)-1-(2-hydroxyphenyl) propan-1-one 2.0 g (14.7 mmol) of 2-hydroxyacetophenone, 1.75 g of 4,5-dimethylfuran-2-carbaldehyde (14.1 mmol), and 10 ml of 25% wt NaOCH$_3$ were reacted in 50 ml of dry THF to give 1.71 g (50%) of chalcone after purification. $^1$H NMR (300 MHz, CDCl$_3$): δ 13.07 (s, 1H), 7.95 (d, J=7.8 Hz, 1H), 7.61 (d, J=15.0 Hz, 1H), 7.51-7.42 (m, 2H), 7.02 (d, d, J=0.9, 8.4 Hz, 1H), 6.94 (d, d, J=1.2, 8.4, 9.0 Hz, 1H), 6.60 (s, 1H), 2.34 (s, 3H), 2.00 (s, 3H).

$^{13}$C NMR (75.5 Hz, CDCl$_3$) δ 193.29, 163.52, 152.60, 148.96, 135.91, 131.22, 129.56, 121.57, 120.22, 118.67, 118.46, 118.43, 115.20, 11.88, 9.68.

HPLCMS (APCI+): m/z=243.1.

Hydrogenation of 1.06 g (4.38 mmol) of chalcone with catalytic amount of 10% Pd/C gives the dihydrochalcone after purification on silica gel chromatography. $^1$H NMR (300 MHz, CD$_3$OD): δ 7.91 (d, d, J=1.8, 8.4 Hz, 1H), 7.50 (d, d, d, J=1.8, 7.2, 9.0 Hz, 1H), 6.97-6.92 (m, 2H), 5.83 (s, 1H), 3.34 (t, J=7.8 Hz, 2H), 2.96 (t, J=7.2 Hz, 2H), 2.13 (s, 3H); 1.87 (s, 3H).

$^{13}$C NMR (75.5 Hz, CD$_3$OD) δ 207.01, 163.31, 152.56, 146.67, 137.33, 131.50, 120.80, 120.18, 119.02, 115.46, 109.61, 37.88, 23.56, 11.10, 9.84.

HPLCMS (APCI+): m/z=245.1.

EXAMPLE 11

1-(2-hydroxyphenyl)-3-(4-methylthiazol-2-yl)propan-1-one 2.27 g (16.7 mmol) of 2-hydroxyacetophenone, 2.0 g of 4-methylthiazole-2-carbaldehyde (15.7 mmol), and 10 ml of 25% wt NaOCH$_3$ were reacted in 50 ml of dry THF to give 0.67 g (17%) of chalcone after purification. $^1$H NMR (300 MHz, CDCl$_3$): δ 12.67 (s, 1H), 7.98-7.95 (m, 1H), 7.80 (d, J=15.3 Hz, 1H), 7.89 (d, J=15.0 Hz, 1H), 7.53 (d, d, J=8.4, 8.4 Hz, 1H), 7.11 9 s, 1H), 7.05 (d, J=8.4 Hz, 1H), 6.97 (d, d, J=7.5, 7.8 Hz, 1H), 2.56 (s, 3H).

$^{13}$C NMR (75.5 Hz, CDCl$_3$) δ 193.04, 163.65, 162.50, 155.71, 136.77, 135.40, 129.95, 123.40, 119.90, 118.99, 118.60, 117.52, 17.14.

HPLCMS (APCI+): m/z=246.1.

Hydrogenation of 1.2 g (4.90 mmol) of chalcone with catalytic amount of 10% Pd/C obtained 0.99 g (81%) of dihydrochalcone after purification on silica gel chromatography (10% EtOAc/hexane). $^1$H NMR (300 MHz, CD$_3$OD): δ 7.93 (d, d, J=1.5, 8.4 Hz, 1H), 7.51 (d, d, d, J=1.5, 7.5, 8.4 Hz, 1H), 6.97-6.96 (m, 1H), 6.93 (s, 1H), 3.61 (t, J=7.2 Hz, 2H), 3.40 (t, J=6.9 Hz, 2H).

$^{13}$C NMR (75.5 Hz, CD$_3$OD) δ 205.69, 171.34, 163.20, 153.11, 137.47, 131.42, 120.77, 120.29, 119.06, 114.50, 103.55, 38.87, 27.90, 16.65.

HPLCMS (API-ES): m/z=248.0.

EXAMPLE 12

1-(2-hydroxyphenyl)-3-(pyridin-2-yl)propan-1-one 2.08 g (15.3 mmol) of 2-hydroxyacetophenone, 1.55 g of 2-pyridine-carboxaldehyde (14.5 mmol), and 10 ml of 25% wt NaOCH$_3$ were reacted in 50 ml of dry THF to give 1.4 g (43%) of chalcone after purification. $^1$H NMR (300 MHz, CDCl$_3$): δ 12.76 (s: 1H), 8.73 (d, J=4.5 Hz, 1H), 8.29 (d, J=15.3 Hz, 1H), 8.06 (d, d, J=1.5, 8.1 Hz, 1H), 7.78 (d, J=15.0 Hz, 1H), 7.77 (d, d, d, J=1.8, 7.5, 9.3, 1H), 7.56-7.50 (m, 2H), 7.37-7.32 (m, 1H), 7.05 (d, J=8.4 Hz, 1H), 7.01-6.94 (m, 1H).

$^{13}$C NMR (75.5 Hz, CDCl$_3$) δ 194.12, 163.66, 152.80, 150.21, 143.14, 137.00, 136.66, 130.28, 125.83, 124.67, 124.29, 120.10, 118.94, 118.51.

HPLCMS (APCI+): m/z=226.1.

Hydrogenation of 1.22 g (4.44 mmol) of chalcone with catalytic amount of 10% Pd/C obtained 0.57 g (46%) of dihydrochalcone after purification on silica gel chromatography (30% EtOAc/hexane). $^1$H NMR (300 MHz, CDCl$_3$): δ 12.29 (s, 1H), 8.52 (d, J=4.8 Hz, 1H), 7.84 (d, d, J=1.5, 8.1 Hz, 1H), 7.61 (d, d, d, J=1.8, 7.5, 9.3 Hz, 1H), 7.45 (d, d, d, J=1.8, 8.7, 9.9 Hz, 1H), 7.25 (d, J=7.8 Hz, 1H), 7.13 (d, d, J=5.7, 7.2 Hz, 1H), 6.98 (d, J=8.4 Hz, 1H), 6.92-6.86 (m, 1H), 3.56 (t, J=7.2 Hz, 2H), 3.25 (t, J=7.2 Hz, 2H).

HPLCMS (API-ES): m/z=228.0.

EXAMPLE 13

1-(2-hydroxyphenyl)-3-(pyridin-4-yl)propan-1-one 2.26 g (16.6 mmol) of 2-hydroxyacetophenone, 1.68 g of 4-pyridine-carboxaldehyde (15.7 mmol), and 10 ml of 25% wt NaOCH$_3$ were reacted in 50 ml of dry THF to give 1.02 g (29%) of chalcone after purification. $^1$H NMR (300 MHz, CDCl$_3$): δ 12.56 (s, 1H), 8.72-8.70 (m, 2H), 7.90 (d, d, J=1.5, 7.8 Hz, 1H), 7.80 (s, 2H), 7.56-7.48 (m, 3H), 7.05 (d, d, J=0.9, 8.4 Hz, 1H), 6.97 (d, d, J=7.2, 7.5 Hz, 1H).

$^{13}$C NMR (75.5 Hz, CDCl$_3$) δ 193.08, 163.64, 150.62, 142.04, 141.70, 136.91, 129.74, 124.45, 122.06, 120.08, 119.05, 118.70.

HPLCMS (APCI+): m/z=226.1.

Hydrogenation of 1.4 g (6.22 mmol) of chalcone with catalytic amount of 10% Pd/C obtained 0.195 g (14%) of dihydrochalcone after purification on silica gel chromatography (30% EtOAc/hexane). $^1$H NMR (300 MHz, CDCl$_3$): δ 12.16 (s, 1H), 8.53-8.51 (m, 2H), 7.73 (d, d, J=1.5, 7.8 Hz, 1H), 7.48 (d, d, d, J=1.8, 7.5, 8.7 Hz, 1H), 7.19-7.17 (m, 2H), 6.99 (d, d, J=0.9, 8.1 Hz, 1H), 6.89 (d, d, d, J=1.2, 7.2, 8.1 Hz, 1H), 3.36 (t, J=7.2 Hz, 2H), 3.07 (t, J=7.5 Hz, 2H).

$^{13}$C NMR (75.5 Hz, CDCl$_3$) δ 204.18, 162.45, 149.93, 149.67, 136.55, 129.57, 123.77, 119.12, 119.00, 118.66, 38.40, 28.95.

HPLCMS (API-ES): m/z=228.0.

EXAMPLE 14

1-(2-hydroxyphenyl)-3-(6-(piperidin-1-yl)pyridin-3-yl)propan-1-one 1.72 g (12.6 mmol) of 2-hydroxyacetophenone, 2.0 g of 6-(piperidin-1-yl)nicotinaldehyde (10.5 mmol), and 10 ml of 25% wt NaOCH$_3$ were reacted in 50 ml of dry THF to give 1.41 g (43.5%) of chalcone after purification. $^1$H NMR (300 MHz, CDCl$_3$): δ 13.10 (s, 1H), 8.39 (d, J=2.4 Hz, 1H), 7.93-7.89 (m, 2H), 7.80 (d, d, J=2.4, 9.0 Hz), 7.51-7.42 (m, 2H), 7.03 (d, d, J=0.9, 8.4 Hz, 1H), 6.94 (d, d, d, J=1.2, 7.2, 8.1 Hz, 1H), 6.68 (d, J=9.0 Hz, 1H), 3.71-3.67 (m, 4H), 1.75-1.67 (m, 6H).

$^{13}$C NMR (75.5 Hz, CDCl$_3$) δ 193.28, 163.55, 159.69, 151.69, 143.34, 135.84, 135.60, 129.35, 120.23, 118.79, 118.64, 118.53, 115.07, 106.47, 45.99, 25.61, 24.64.

HPLCMS (APCI+): m/z=309.2.

Hydrogenation of 0.5 g (1.62 mmol) of chalcone with catalytic amount of 10% Pd/C obtained 0.33 g (66%) of dihydrochalcone after purification on silica gel chromatography (5% EtOAc/hexane). $^1$H NMR (300 MHz, CD$_3$OD): δ 7.97 (d, J=0.3 Hz, 1H), 7.88 (d, d, J=1.8, 8.4 Hz, 1H), 7.51-7.45 (m, 2H), 6.95-6.89 (m, 2H), 6.75 (d, J=8.1 Hz, 1H), 3.47-3.45 (m, 4H), 3.34 (t, J=7.2 Hz, 2H), 2.92 (t, J=7.2 Hz, 2H).

$^{13}$C NMR (75.5 Hz, CD$_3$OD) δ 207.28, 163.33, 160.16, 147.92, 139.59, 137.34, 131.55, 126.46, 120.83, 120.20, 119.04, 109.25, 27.34, 26.57, 25.74.

HPLCMS (API-ES): m/z=311.1.

EXAMPLE 15

1-(2-hydroxyphenyl)-3-(thiazol-2-yl)propan-1-one 2.29 g (16.8 mmol) of 2-hydroxyacetophenone, 1.8 g of thiazole-2-carbaldehyde (15.9 mmol), and 10 ml of 25% wt NaOCH$_3$ were reacted in 50 ml of dry THF to give 0.254 g (27%) of chalcone after purification. $^1$H NMR (300 MHz, CDCl$_3$): δ 12.62 (s, 1H), 8.08-7.94 (m, 4H), 7.57-7.51 (m, 2H), 7.06 (d, d, J=1.2, 8.4 Hz, 1H), 6.98 (d, d, d, J=1.2, 7.2, 8.1 Hz, 1H).

$^{13}$C NMR (75.5 Hz, CDCl$_3$) δ 192.97, 163.67, 163.45, 145.16, 136.89, 135.24, 129.91, 124.11, 122.33, 119.87, 119.06, 118.66.

HPLCMS (APCI+): m/z=232.1.

Hydrogenation of 0.27 g (1.16 mmol) of chalcone with catalytic amount of 10% Pd/C obtained 0.26 g (27%) of dihydrochalcone after purification on silica gel chromatography (20% EtOAc/hexane). $^1$H NMR (300 MHz, CD$_3$OD): δ 7.83 (d, d, J=1.8, 8.7 Hz, 1H), 7.63 (d, J=3.3 Hz, 1H), 7.46-7.38 (m, 2H), 6.90-6.85 (m, 2H), 3.55 (t, J=6.3 Hz, 2H), 3.39 (t, J=6.6 Hz, 2H).

$^{13}$C NMR (75.5 Hz, CD$_3$OD) δ 205.56, 171.57, 163.11, 142.96, 137.58, 131.43, 120.68, 120.39, 120.37, 119.20, 38.37, 27.77.

HPLCMS (API-ES): m/z=234.0.

EXAMPLE 16

3-(6-chloropyridin-3-yl)-1-(2-hydroxyphenyl)prop-2-en-1-one 2.08 g (15.3 mmol) of 2-hydroxyacetophenone, 2.05 g of 6-chloronicotinaldehyde (14.5 mmol), and 10 ml of 25% wt NaOCH$_3$ were reacted in 50 ml of dry THF to give 0.55 g (15%) of chalcone after purification. $^1$H NMR (300 MHz, CDCl$_3$): δ 12.61 (s, 1H), 8.66 (d, J=2.4 Hz, 1H), 7.97-7.92 (m, 2H), 7.90 (D, J=15.9 Hz, 1H), 7.71 (d, J=15.6 Hz, 1H), 7.55 (d, d, d, J=1.5, 7.2, 8.7 Hz, 1H), 7.43 (d, J=8.1 Hz, 1H), 7.06 (d, d, J=0.9, 8.4 Hz, 1H), 6.98 (d, d, d, J=1.2, 7.5, 8.1 Hz, 1H).

$^{13}$C NMR (75.5 Hz, CDCl$_3$) δ 192.84, 163.72, 153.18, 149.97, 139.93, 137.06, 136.87, 129.61, 129.42, 124.69, 122.63, 119.71, 119.05, 118.80.

HPLCMS (APCI+): m/z=260.1.

EXAMPLE 17

1-(2-hydroxy-4-(methoxy)phenyl)-3-(6-methoxypyridin-3-yl)propan-1-one 4.18 g (21.3 mmol) of 1-(2-hydroxy-4-(methoxymethoxy)phenyl)ethanone, 2.8 g of 6-methoxy-3-pyridine-carboxaldehyde (20.4 mmol), and 1.8 g (32.1 mmol) of KOH were reacted in 60 ml of EtOH and 20 ml of H$_2$O ml to give 2.18 g (34%) of chalcone after purification. $^1$H NMR (300 MHz, CDCl$_3$): δ 13.27 (s, 1H), 8.42 (d, J=2.4 Hz, 1H), 7.95-7.82 (m, 3H), 7.50 (d, J=15.6 Hz, 1H), 6.83 (d: J=8.7 Hz, 1H), 6.67 (d, J=2.7 Hz; 1H), 6.61 (d, d, J=2.4, 9.0 Hz, 1H), 5.25 (s, 2H), 4.02 (s, 3H), 3.51 (s, 3H).

$^{13}$C NMR (75.5 Hz, CDCl$_3$) δ 191.62, 166.27, 165.56, 163.72, 149.14, 141.03, 136.65, 131.18, 124.21, 119.15, 114.88, 111.67, 108.26, 104.05, 94.08, 56.39, 53.92.

HPLCMS (API-ES): m/z=316.0.

Hydrogenation of 1.78 g (5.65 mmol) of chalcone with catalytic amount of 10% Pd/C obtained 1.2 g (67%) of dihydrochalcone and 2-(1-hydroxy-3-(6-methoxypyridin-3-yl)propyl)-5-(methoxymethoxy)phenol after purification on silica gel chromatography (15% EtOAc/hexane).

Dihydrochalcone: $^1$H NMR (300 MHz, CDCl$_3$): δ 12.60 (s, 1H), 8.05 (d, J=2.4 Hz, 1H), 7.64 (d, J=9.0 Hz, 1H), 7.48 (d, d, J=2.4, 8.7 Hz, 1H), 6.70 (d, J=8.4 Hz, 1H), 6.61 (d, J=2.4 Hz, 1H), 6.51 (d, d, J=2.4, 8.7 Hz, 1H), 5.21 (s, 2H), 3.92 (s, 3H), 3.48 (s, 3H), 3.22 (t, J=7.5 Hz, 2H), 2.99 (t, J=7.5 Hz, 2H).

$^{13}$C NMR (75.5 Hz, CDCl$_3$) δ 203.12, 165.00, 163.59, 162.91, 146.06, 139.06, 131.40, 128.79, 114.23, 110.66, 108.27, 103.79, 94.01, 91.26, 60.35, 56.35, 39.37, 26.39.

HPLCMS (API-ES): m/z=318.0.

2-(1-hydroxy-3-(6-methoxypyridin-3-yl)propyl)-5-(methoxymethoxy)phenol: $^1$H NMR (300 MHz, CDCl$_3$): δ 7.99 (d, d, J=0.6, 2.4 Hz, 1H), 7.44 (d, d, J=2.4, 8.4 Hz, 1H), 6.83 (d, J=8.4 Hz, 1H), 6.70 (d, d, J=0.6, 9.0 Hz, 1H), 6.61 (d, J=3.0 Hz, 1H), 6.52 (d, d, J=2.7, 8.4 Hz, 1H), 5.15 (s, 2H), 4.77 (d, d, J=5.4, 8.1 Hz, 1H), 3.92 (s, 3H), 3.48 (s, 3H), 2.71-2.64 (m, 2H), 2.26-2.16 (m, 1H), 2.09-2.02 (m, 1H).

$^{13}$C NMR (75.5 Hz, CDCl$_3$) δ 162.72, 157.96, 156.68, 145.82, 139.21, 129.37, 127.70, 121.17, 110.62, 107.62, 105.30, 94.42, 74.17, 56.00, 53.53, 38.31, 28.05.

HPLCMS (API-ES): m/z=320.1.

EXAMPLE 18

1-(2,4-dihydroxyphenyl-3-(6-methoxypyridin-3-yl)propan-1-one

To a solution of 1-(2-hydroxy-4-(methoxymethoxy)phenyl)-3-(6-methoxypyridin-3-yl)propan-1-one (1.62 g, 5.11 mmol) in CH$_3$CN (30 ml) at room temperature was added TFA (2 ml) dropwise, two drops of water. The reaction was stirred at same temperature for 8 h. Aqueous 1N NaOH was added to the reaction mixture until pH=7. The aqueous was extracted with 100 ml EtOAc, and the organic layers were combined. The organic layer was washed with brine, dried (Na$_2$SO$_4$) and concentrated. The residue was purified by silica gel chromatography (15% EtOAc/Hexane) to provide 0.5 g (35%) of white solid.

$^1$H NMR (300 MHz, CD$_3$OD): δ 8.00 (s, 1H), 7.72 (d, J=9.0 Hz, 1H), 7.61 (d, J=2.4, 8.4 Hz, 1H), 6.72 (d, J=8.7 Hz, 1H), 6.33 (d, d, J=2.4, 9.0 Hz), 6.23 (d, J=2.4 Hz, 1H), 3.86 (s, 3H), 3.24 (t, J=7.2 Hz, 2H), 2.93 (t, J=7.2 Hz, 2H).

13C NMR (75.5 Hz, CD$_3$OD) δ 204.8, 166.4, 164.3, 147.1, 141.0, 133.6, 130.9, 114.1, 111.2, 109.1, 103.6, 54.1, 40.0, 27.6.

HPLCMS (APCI+): m/z=274.3.

EXAMPLE 19

1-(2-hydroxy-4-((3R,4S,5S,6R)-3,4,5-trihydroxy-6-(hydroxymethyl)tetrahydro-2H-pyran-2-yloxy)phenyl)-3-(6-methoxypyridin-3-yl)propan-1-one To a solution of 1-(2,4-dihydroxyphenyl-3-6-methoxypyridin-3-yl)propan-1-one (0.234 g, 0.86 mmol) in 1:1 1N KCl: 1N NaHCO3 (10 ml) at room temperature was added D-glucopyranosyl bromide (0.7 g, 1.7 mmol, 10 ml in dry CH$_2$CN) dropwise. The mixture was refluxed for 24 h under N$_2$. After the addition of water, the mixture was extracted 3× with CH$_2$Cl$_2$. The organic layers were combined and washed with 1N HCl, water, brine, dried (Na$_2$SO$_4$) and concentrated. Silica gel chromatography purification (35% EtOAc/Hexane) provided 0.25 g (48%) sugar dihydrochalcone, which was de-protected by NaOMe in MeOH at room temperature provided 88 mg (49%) final glycosylated dihydrochalcone product.

Intermediate A: $^1$H NMR (300 MHz, CDCl$_3$): δ 12.63 (s, 1H), 8.08 (d, J=2.1 Hz, 1H), 7.68 (d, J=9.0 Hz, 1H), 7.51 (d, d, J=2.7, 8.7 Hz, 1H), 6.85-66.80 (d, J=8.7 Hz, 1H), 6.57 (d, J=2.4 Hz, 1H), 6.53 (d, d, J=3.9, 6.3 Hz, 1H), 5.36-5.29 (m, 2H), 5.24-5.13 (m, 2H), 4.35-4.25 (m, 1H), 4.21-4.13 (m, 1H), 3.95 (s, 3H), 3.25 (t, J=7.2 Hz, 2H), 3.03 (t, J=7.2 Hz, 2H).

HPLCMS (APCI+): m/z=604.0.

Final product: $^1$H NMR (300 MHz, CD$_3$OD): δ 8.02 (d, J=1.8 Hz, 1H): 7.85 (d, J=9.0 Hz, 1H), 7.63 (d, d, J=2.4, 8.4 Hz, 1H), 6.74 (d, d, J=0.6, 8.4 Hz, 1H), 6.65 (d, d, J=2.4, 8.7 Hz, 1H), 6.61 (d, J=2.4 Hz, 1H), 4.96 (d, J=7.5 Hz, 1H), 3.92 (d, J=3.0 Hz, 1H), 3.84-3.71 (m, 4H), 3.60 (d, d, J=3.3, 9.6, Hz, 1H), 3.37-3.29 (m, 2H), 2.99 (t, J=7.2 Hz, 2H).

$^{13}$C NMR (75.5 Hz, CD$_3$OD) δ 205.4, 165.7, 165.2, 164.4, 147.1, 140.9, 133.2, 130.8, 115.9, 111.2, 109.5, 105.1, 101.9, 77.1, 74.7, 72.1, 70.1, 62.3, 54.0, 40.3, 27.4.

HPLCMS (ES+): m/z=436.1.

EXAMPLE 20

1-(2-hydroxy-4-(2-hydroxyethoxy)phenyl)-3-(6-methoxypyridin-3-yl)propan-1-one

To a solution of 2.4 dihydroxyacetophenone (1.58 g, 10.4 mmol) in dry acetone (30 ml) at room temperature was added potassium carbonate (1.56 g, 27.8 mmol), (2-bromoethoxy)(tert-butyl)dimethylsilane. The solution was reflux for 7 hrs, then pour into water. Aqueous layer was extracted with 3× EtOAc and the organic layers were combined. The organic layer was washed with 1N HCl, water, brine, dried (Na$_2$SO$_4$) and concentrated. Chromatography purification obtained 0.36 g of intermediate A and 0.58 g of intermediate B.

In a 100 ml round-bottom flask, 0.36 g of intermediate A (1.80 mmol), 0.25 g of 6-methoxynicotinaldehyde (1.80 mmol) in 10 ml EtOH was treated 0.154 g of KOH (2.75 mmol) in 5 ml water at room temperature. The reaction was stirred at room temperature for 7 hrs and poured into water. Adjusted pH=7 by 1NHCl and extracted with EtOAc. The organic layer was washed three times with water, brine, dried (Na$_2$SO$_4$), and concentrated. The chalcone (0.18 g, 0.57 mmol) was then hydrogenated in 2:1 THF:MeOH with catalytic amount of 10% Pd/C obtained 0.15 g (83%) of final product.

Intermediate A: $^1$H NMR (300 MHz, CDCl$_3$): δ 12.6 (s, 1H), 7.54 (d, J=9.0 Hz, 1H), 6.37 (d, d, J=2.4, 9.0 Hz, 1H), 6.34 (d, d, J=2.4, 8.7 Hz, 1H), 4.02 (t: J=4.8 Hz, 2H), 3.88 (t, J=4.2 Hz, 2H), 2.46 (s, 3H).

HPLCMS (ES+): m/z=196.9.

Intermediate B: $^1$H NMR (300 MHz, CDCl$_3$): δ 12.6 (s, 1H), 7.53 (d, J=8.7 Hz, 1H), 6.37-6.36 (m, 2H), 3.97 (1, J=4.5 Hz, 2H), 3.87 (t, J=4.5 Hz, 2H), 2.45 (s, 3H), 0.81 (s, 9H), 0.00 (s, 6H).

Final product: $^1$H NMR (300 MHz, CD$_3$OD): δ 8.00 (d, J=0.3 Hz, 1H), 7.79 (d, J=9.0 Hz, 1H), 7.61 (d, d, J=2.4, 8.4 Hz, 1H), 6.73 (d, J=8.4 Hz, 1H), 6.51 (d, d, J=2.4, 9.0 Hz, 1H), 6.43 (d, J=2.4 Hz, 1H), 4.08 (t, J=4.2 Hz, 2H), 3.93-3.85 (m, 5H), 3.31-3.21 (t, J=7.5 Hz, 2H), 2.97 (t, J=7.2 Hz, 2H).

$^{13}$C NMR (75.5 Hz, CD$_3$OD) δ 205.1, 166.9, 166.2, 164.4, 147.1, 140.9, 133.2, 130.9, 114.8, 111.2, 108.7, 102.5, 70.9, 61.3, 54.0, 40.1, 27.5.

HPLCMS (ES+): m/z=318.0.

EXAMPLE 21

4-(3-(2-hydroxyphenyl)-3-oxopropyl)pyridinium chloride

A reaction flask equipped with a mechanical stirrer, thermometer, nitrogen inlet and a cooler was charged with 250 ml of water, sodium bicarbonate (35.3 g, 420 mmol) and of 85% sodium dithionite (36.9 g, 180 mol). The mixture was stirred for 3 minutes. Then an amount of 300 ml of THF was added. During 45 minutes, 4-(3-(2-hydroxyphenyl)-3-oxoprop-1-enyl)pyridinium bromide (18.4 g, purity 98.5%, 59.2 mmol) was added in small portions at room temperature while stirring vigorously. An exothermic reaction was noticed. An amount of 100 ml of 10% Na$_2$CO$_3$ solution was added and the mixture was stirred vigorously during 1 hour.

The mixture was poured into a separation funnel and the THF layer was collected. The water layer was extracted with ethyl acetate (3×100 ml) and combined with the THF layer. The combined organic layers were washed with brine (50 ml), dried over anhydrous MgSO$_4$, and concentrated in vacuo. The obtained residue was solved in absolute ethanol (75 ml) and cooled to −5° C. While stirring HCl gas (7.2 g, 197 mmol) was passed through the mixture. A white precipitate was formed. Stirring continued for another 30 min. at −5° C. The precipitate was filtrated and washed with MTBE (10 ml). After drying in a vacuum oven at 40° C. an amount of 14.74 g (55.9 mmol) of the desired product was obtained with a purity of >99%. The yield was 94%.

1H-NMR (solvent DMSO-d6): 3.22 (t, J=7.2, 2H); 3.65 (t, J=7.2, 2H); 6.94 (t, J=7.8, 1H); 7.02 (d, J=8.1, 1H); 7.50 (t, J=7.8, 3H): 7.88 (d, J=8.1 1H); 8.1 (d, J=6.6, 2H); 8.83 (d, J=6.6, 2H), 11.63 (broad, 1H).

13C-NMR (decoupled, solvent DMSO-d6): 203.0, 162.2, 160.1, 141.0, 135.8, 130.5, 127.0, 120.8, 119.1, 117.7, 38.9, 29.3 δppm.

EXAMPLE 22

Taste test data of some compounds are shown below. The taste testing was made by a panel of experienced tasters.

| Example | Structure | Taste results in water |
|---|---|---|
| 1 | 2'-hydroxyphenyl ketone with propyl chain to 5-position of 2-methoxypyridine | 5 ppm, very weak sweet, 20 ppm weakly sweet, 100 ppm very strong sweet, weak bitter taste |
| 3 | 2'-hydroxyphenyl ketone with propyl chain to 3-position of 2-methoxypyridine | Very weak sweet at 1 ppm, 10 ppm, 50 ppm bitter, weakly sweet and burning |
| 2 | 2'-hydroxyphenyl ketone with propyl chain to 2-position of 6-methoxypyridine | Slightly sweet/bitter at 10 ppm, sweet, bitter, slight fruity at 100 ppm. |
| 6 | 2'-hydroxyphenyl ketone with propyl chain to 3-position of 5-methylisoxazole | 0.1 ppm, slightly bitter, 1 ppm, slightly bitter, weakly sweet, 10 ppm, brothy, umami, soapy, irritating, garlic, 100 ppm, umami, bitter, soapy, garlic |
| 4 | 2'-hydroxyphenyl ketone with propyl chain to 5-position of 4-methylthiazole | 0.1 to 1 ppm, petroleum, sulfur, 10 ppm very weak sweet, brothy, 100 ppm sweet, brothy, gassy, bitter, linger |
| 7 | 2'-hydroxyphenyl ketone with propyl chain to 3-pyridyl | 0.1 ppm, nothing, 1 ppm, very weak sweet, astringent, 10 ppm, waxy, delayed sweet, astringent, 100 ppm, weak sweet, chemical, bitter |
| 8 | 2'-hydroxyphenyl ketone with propyl chain to 2-furyl | 0.01 ppm, nothing, 0.1 ppm, soap, delayed sweet. 1 ppm, soap, umami, bitter, 10 ppm, licorice aroma, soapy, weak sweet, bitter, vegetable, terpen, 100 ppm, bitter, licorice aroma, weak sweet, celery, umami, brothy |
| 10 | 2'-hydroxyphenyl ketone with propyl chain to 3-position of 2,5-dimethylfuran | 0.01 ppm, nothing, 0.1 ppm, floral, soapy, 1 ppm. floral, soap, astringent, piney, 10 ppm. weak bitter, vegetable, piney, astringent, 100 ppm, slightly sweet, bitter, piney, vegetable, sour |
| 15 | 2'-hydroxyphenyl ketone with propyl chain to 2-thiazolyl | 0.0.1 ppm, 0.1 ppm, delayed umami aftertaste, 1 ppm, weak plastic, soap, umami, astringent. 10 ppm, astringent. strong umami, weak soap, slight bitter, 100 ppm, bitter. umami |

| Example | Structure | Taste results in water |
|---|---|---|
| 11 | 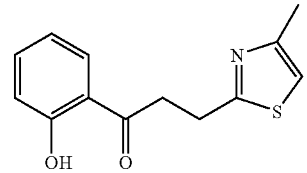 [SMILES: Cc1csc(CCC(=O)c2ccccc2O)n1] | 0.01 ppm. nothing, 0.1 ppm, very weak bitter, 1 ppm, astringent, bitter, 10 ppm, bitter, astringent, 100 ppm, bitter, terpen, weak sweet |
| 13 | 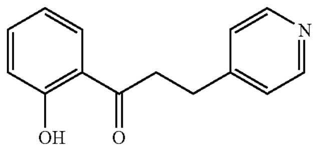 [SMILES: O=C(CCc1ccncc1)c1ccccc1O] | 0.01 ppm to 0.1 ppm, nothing, 1 ppm, weak sweet, 10 ppm. sweet, 100 ppm, very sweet, licorice linger |
| 12 | 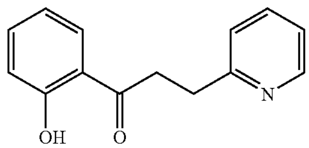 [SMILES: O=C(CCc1ccccn1)c1ccccc1O] | 1 ppm, umami, 10 ppm, high umami like taste, 100 ppm, strong umami, slightly bitter. |
| 18 | 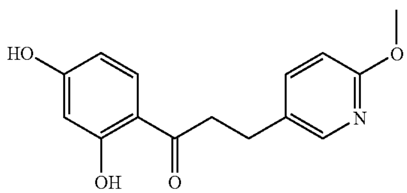 [SMILES: COc1ccc(CCC(=O)c2ccc(O)cc2O)cn1] | 100 ppm, sweet |

EXAMPLE 23

Evaluation Data on the Compound of Example 13, showing how it Modifies a Flavor in Water and in Application.

Strawberry A=candy strawberry. Strawberry B=green strawberry. Strawberry C=floral strawberry. Strawberry D=fruity strawberry. Vanillic Flavor A=vanillic, milky, creamy flavor:

| Application | Flavor | Flavorist Evaluation |
|---|---|---|
| Water | Strawberry A @ 0.2% | Green, candy-like, moderate lactone character, overripe rotten |
| Water | Strawberry A @ 0.2% + 20 ppm compound 13 | Green character remains but softer, sweeter character removing the candy-like edge associated with the flavor. Character is juicier, and more of a strawberry & cream with some plastic off-notes. |
| Water | Strawberry B @ 0.2% | Slightly green strawberry |
| Water | StrawberryB @ 0.2% + 20 ppm compound 13 | Sweeter, less green, jammer, maltol-like note, some plastic off-notes |
| Water | Strawberry C @ 0.2% | Slightly green, floral, kool-aid type strawberry |
| Water | Strawberry C @ 0.2% + 20 ppm compound 13 | Less green, less floral, burnt sugar caramel note, strawberry character and coumarin-type character is intensified. |
| Water | Sweetness Improver Flavor A in 25% sugar reduction Grape Type Drink | Sweet grape character, some of the acidic middle profile was suppressed, lingering sweet character not seen in target |
| Water | Sweetness Improver Flavor A + 5 ppm compound 13 in 25% sugar reduction Grape Type Drink | Sweet grape character with the acidic middle regained, enhanced sweet character without the lingering, more of an abrupt sugar-like finish to the flavor profile |
| Vanilla ice cream 8% vegetable fat ice cream | Vanilla flavour A @ 0.5% | vanillic, milky, creamy |
| Vanilla ice cream 8% vegetable fat ice cream | Vanilla flavour A @ 0.5% + 10 ppm of compound 13 | creamy, vanillic, sweet, slightly cooked |
| Vanilla ice cream 8% vegetable fat | Vanilla flavour A @ 0.5% + 15 ppm of compound | creamy, sweet, vanillic, lingering sweet vanilla aftertaste |

| Application | Flavor | Flavorist Evaluation |
|---|---|---|
| ice cream | 13 | |
| Vanilla ice cream 8% vegetable fat ice cream | Vanilla flavour A @ 0.5% + 30 ppm of compound 13 | sweet, vanillic, lingering sweet vanilla aftertaste |
| Strawberry yoghurt 3% fat, 7% sugar | Strawberry flavour D @ 0.1% | Fruity, green, fresh, jammy, floral |
| Strawberry yoghurt 3% fat, 7% sugar | Strawberry flavour D @ 0.1% + 10 ppm of compound 13 | Fruity, slightly fermented, caramellic, green |
| Strawberry yoghurt 3% fat, 7% sugar | Strawberry flavour D @ 0.1% + 25 ppm of compound 13 | Fruity, sweet, fermented, caramellic, apple like |
| Strawberry yoghurt 3% fat, 7% sugar | Strawberry flavour D @ 0.1% + 50 ppm of compound 13 | Fermented, sweet, brown, caramellic, overripe banana |
| Water | 7% sugar + 20 ppm of compound 13 | Sweeter than 7% sugar, little floral, fuller, slight longer sweet character, backend slightly delayed, sweeter than 7% with a delayed onset |
| Water | 7% sugar + 50 ppm of compound 13 | Sweeter than above, very close to 9% sugar- just a very small difference, slight plastic |
| Water | 7% sugar with 0.105% Citric acid + 20 ppm of compound 13 | Sweeter than control, not effecting acidity, nice backend, sweeter brown notes, cotton candy |
| Water | 7% sugar with 0.105% Citric acid + 50 ppm of compound 13 | Sweeter than sample at 20 ppm, musty, clean, not that lingering |
| 2% milk | 20 ppm compound 13 | Slight change in profile, Sweeter than control (2% milk) |
| Cereal | 50% reduced sugar + 20 ppm of compound 13 | Not lingering, more brown notes, roasted, sweeter than control |
| Cereal | 50% reduced sugar + 50 ppm of compound 13 | Sweeter than 50% reduced control, better performance, sweeter than 20 ppm, maybe slight offnote, close to target |
| Cereal | 50% reduced sugar + 20 ppm of compound 13 + 100 ppm of Sweet Flavor B | Nice, works well, more close to sugar taste, clearly sweeter than 50% red, Sweeter, close to target, higher late sweetness and longer sweetness than above |

EXAMPLE 24

Testing of Compound of Example 21 (Hydrochloride Salt of Example 13).

The sweet isointensity was tested against a variety of sugar solutions by a testing panel. The following results were found:
30 ppm isosweet to 0.75% sucrose
35 ppm isosweet to 1.0% sucrose
40 ppm isosweet to 1.25% sucrose It was additionally found that 30 ppm of the compound+ 7% sucrose pushes the sweetness equivalent to 8.5% sucrose.

EXAMPLE 25

Testing of the Compound of Example 21 in Yoghurt

5% sugar and 25 ppm of the compound were added to plain non-fat yoghurt. A trained panel compared this to a series of plain non-fat yoghurts to which 5%, 6% 7% and 8% sugar had been added.

The panel found that the treated yoghurt was isosweet to 6.5% sugar, an appreciable increase in sweetness.

While the compounds, methods of providing flavors and orally receivable and ingestable products have been described above in connection with illustrative embodiments, it is to be understood that other similar embodiments may be used or modifications and additions may be made to the described embodiments for performing the same function without deviating therefrom. Further, all embodiments disclosed are not necessarily in the alternative, as various embodiments of the invention may be combined to provide the desired characteristics. Variations can be made by one having ordinary skill in the art without departing from the spirit and scope of the invention. Therefore, the compounds, methods and products should not be limited to any single embodiment, but rather construed in breadth and scope in accordance with the recitation of the attached claims.

We claim:

1. A method of providing flavor to a composition adapted to be received orally, comprising adding to the composition a salt of at least one compound of the formula:

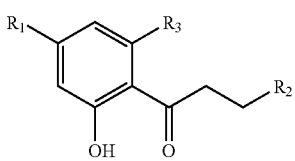

wherein $R^1$ comprises H, OH, O(CH$_2$)$_2$OH, OCH$_2$OCH$_3$ or

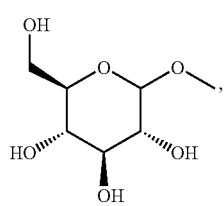

wherein R² comprises a heterocyclic moiety selected from:

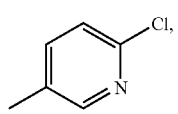 (i)

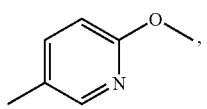 (ii)

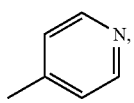 (iii)

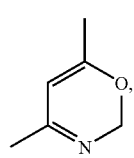 (iv)

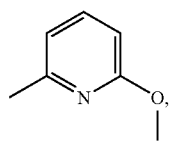 (v)

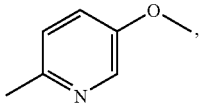 (vi)

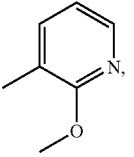 (vii)

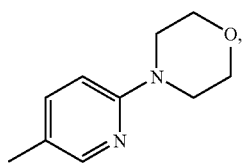 (viii)

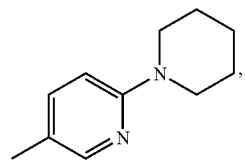 (ix)

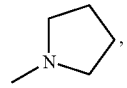 (x)

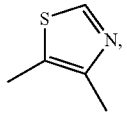 (xi)

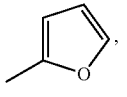 (xii)

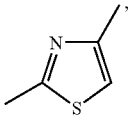 (xiii)

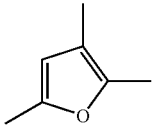 (xiv)

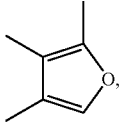 (xv)

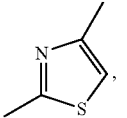 (xvi)

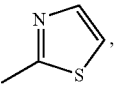 (xvii)

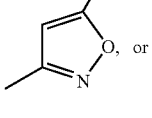 (xviii)

(xix)

(xx)

wherein $R_3$ comprises H or OH; and wherein the salt is at least one of $K^+$, $NH_4^+$, $Na^+$, $Ca^{2+}$, $Mg^{2+}$, $Al^{3+}$, $Zn^{2+}$, hydrochloride or hydrobromide salt.

2. The method according to claim 1, wherein R² comprises at least one of the moieties (iii), (iv), (vii), (viii), (xiii), (xvii), or (xviii).

3. A salt of the compound of the formula:

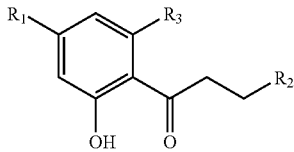

wherein R¹ comprises H, OH, O(CH₂)₂OH, OCH₂OCH₃, or

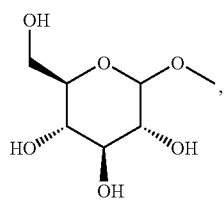

wherein R² comprises a moiety selected from:

(iii)
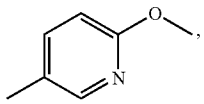

(iv)
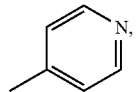

(vi)
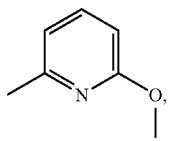

(viii)
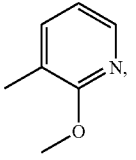

(x)
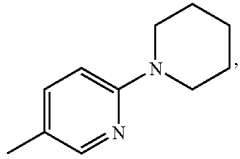

(xii)
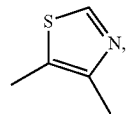

(xiii)
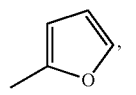

-continued (xiv)
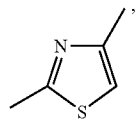

(xvi)
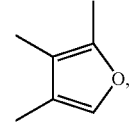

(xvii)
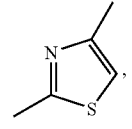

(xviii)
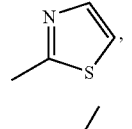

(xix)
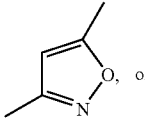, or (xx)
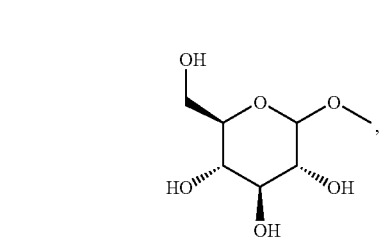

and wherein R³ comprises H or OH;
such that
(a) when R¹ comprises H, R² comprises a moiety selected from (iii), (iv), (vi), (viii), (x), (xii), (xiii), (xiv), (xvi), (xvii), (xviii), (xix), or (xx);
(b) when R¹ comprises OH, R² comprises moiety (iii) or (iv);
(c) when R¹ comprises —OCH₂OCH₃, R² comprises moiety (iii) or (iv);
(d) when R¹ comprises

[structure]

R² comprises moiety (iii) or (iv);
(e) when R¹ comprises —OCH₂CH₂OH, R² comprises moiety (iii); and
wherein the salt is at least one of K⁺, NH₄⁺, Na⁺, Ca²⁺, Mg²⁺, Al³⁺, Zn²⁺, hydrochloride or hydrobromide salt.

4. The compound of claim 3, wherein said compound comprises 1-(2-hydroxyphenyl)-3-(pyridin-4-yl)propan-1-one or a hydrochloride or hydrobromide salt thereof.

5. A method of reducing the natural or artificial sweetener content of a sweetener-containing consumable product while maintaining sweetness, comprising adding a sweetness-enhancing quantity of 1-(2-hydroxyphenyl)-3-(pyridin-4-yl) propan-1-one or a hydrochloride or hydrobromide salt thereof to said product.

6. The method according to claim 5, comprising adding said 1-(2-hydroxyphenyl)-3-(pyridin-4-yl)propan-1-one or a hydrochloride or hydrobromide salt thereof and at least one other sweetness-enhancing compound to said product.

7. An orally-receivable product comprising ancillary product compounds and a salt of at least one flavor providing compound of the formula:

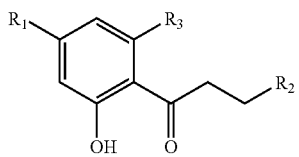

wherein $R^1$ comprises H, OH, O(CH$_2$)$_2$OH, OCH$_2$OCH$_3$ or

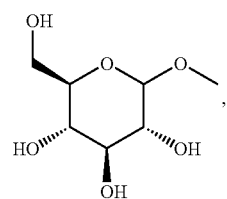

wherein $R^2$ comprises a heterocyclic moiety selected from:

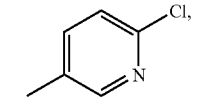 (i)

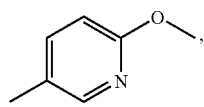 (ii)

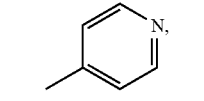 (iii)

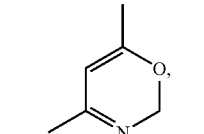 (iv)

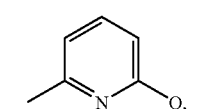 (v)

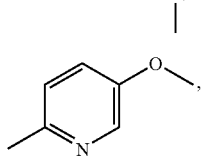 (vi)

(vii)

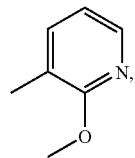 (viii)

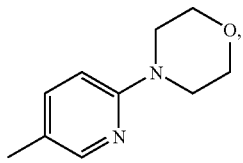 (ix)

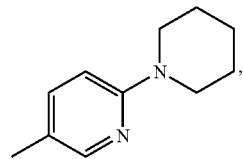 (x)

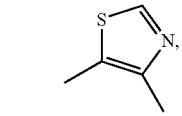 (xi)

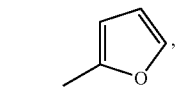 (xii)

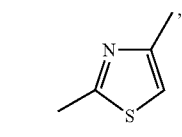 (xiii)

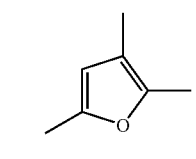 (xiv)

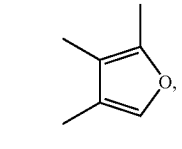 (xv)

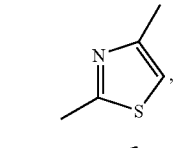 (xvi)

(xvii)

(xviii)

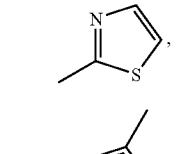, or (xix)

-continued (xx)
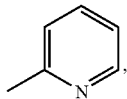

wherein R₃ comprises H or OH, and wherein the salt is at least one of K⁺, NH₄⁺, Na⁺, Ca²⁺, Mg²⁺, Al³⁺, Zn²⁺, hydrochloride or hydrobromide salt.

8. The orally-receivable product of claim 7, wherein said flavor-providing compound comprises 1-(2-hydroxyphenyl)-3-(pyridin-4-yl)propan-1-one or a hydrochloride or hydrobromide salt thereof.

9. The orally-receivable product of claim 7, wherein said flavor-providing compound comprises 1-(2-hydroxyphenyl)-3-(pyridin-4-yl)propan-1-one or a hydrochloride or hydrobromide salt thereof, and at least one other sweetness-enhancing compound.

10. The orally-receivable product of claim 7, wherein the product is selected from the group consisting of food products, food additives, nutraceuticals, pharmaceuticals, medicaments, beverages, beverage forms requiring reconstitution, tobacco products, chewing gum, oral care products, oral hygiene products, and combinations thereof.

11. A sweetener-containing consumable product comprising:

a sweetener, ancillary product compounds, and a salt of at least one flavor providing compound of the formula:

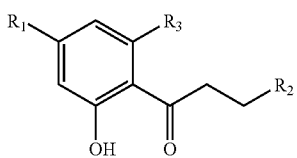

wherein R¹ comprises H, OH, O(CH₂)₂OH, OCH₂OCH₃ or

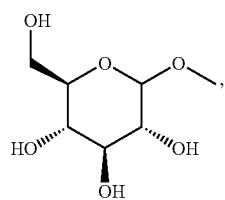

wherein R² comprises a heterocyclic moiety selected from:

(i)
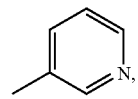

(ii)
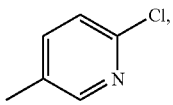

-continued (iii)
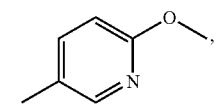

(iv)
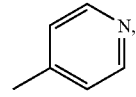

(v)
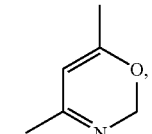

(vi)
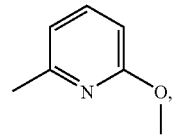

(vii)
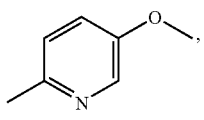

(viii)
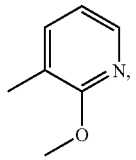

(ix)
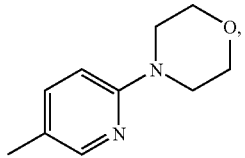

(x)
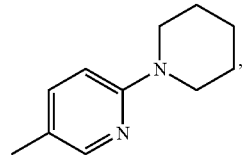

(xi)
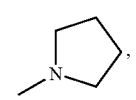

(xii)
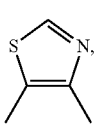

(xiii)
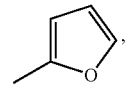

(xiv)
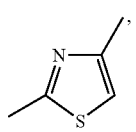

-continued (xv) 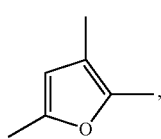

(xvi) 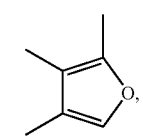

(xvii) 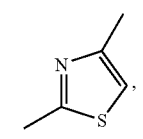

(xviii) 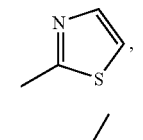

(xix) 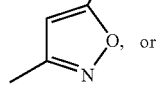 or (xx) 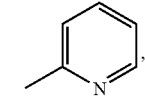

wherein $R_3$ comprises H or OH, and wherein the salt is at least one of $K^+$, $NH_4^+$, $Na^+$, $Ca^{2+}$, $Mg^{2+}$, $Al^{3+}$, $Zn^{2+}$, hydrochloride or hydrobromide salt.

12. The sweetener-containing consumable product of claim 11, wherein said flavor-providing compound comprises 1-(2-hydroxyphenyl)-3-(pyridin-4-yl)propan-1-one or a hydrochloride or hydrobromide salt thereof.

13. The sweetener-containing consumable product of claim 12, wherein said flavor providing compound comprises 1-(2-hydroxyphenyl)-3-(pyridin-4-yl)propan-1-one or a hydrochloride or hydrobromide salt thereof and at least one other sweetness-enhancing compound.

14. The sweetener-containing consumable product of claim 11, wherein the product is selected from the group consisting of food products, food additives, nutraceuticals, pharmaceuticals, medicaments, beverages, beverage forms requiring reconstitution, tobacco products, chewing gum, oral care products, oral hygiene products, and combinations thereof.

15. A compound, including salts thereof, of the formula:

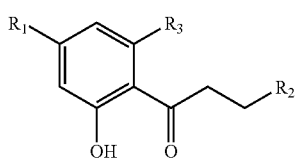

wherein $R^1$ comprises H, OH, O(CH$_2$)$_2$OH, OCH$_2$OCH$_3$, or

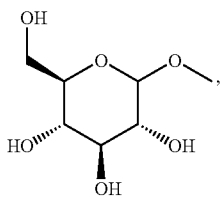

wherein $R^2$ comprises a moiety selected from:

(iii) 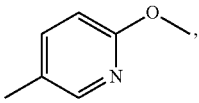

(iv) 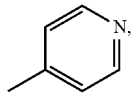

(vi) 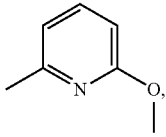

(viii) 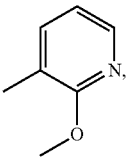

(x) 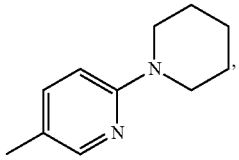

(xii) 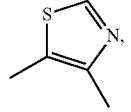

(xiii) 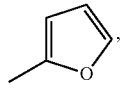

(xiv) 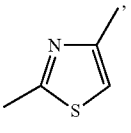

(xvi) 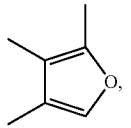

-continued

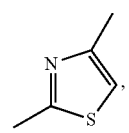 (xvii)

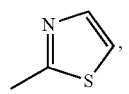 (xviii)

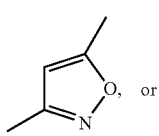 or (xix)

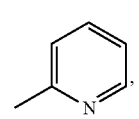 (xx)

and wherein $R^3$ comprises H or OH;
such that
(a) when $R^1$ comprises H, $R^2$ comprises a moiety selected from (iii), (iv), (vi), (viii), (x), (xii), (xiii), (xiv), (xvi), (xvii), (xviii), (xix), or (xx);
(b) when $R^1$ comprises OH, $R^2$ comprises moiety (iii) or (iv);
(c) when $R^1$ comprises —OCH$_2$OCH$_3$, $R^2$ comprises moiety (iii) or (iv);
(d) when $R^1$ comprises

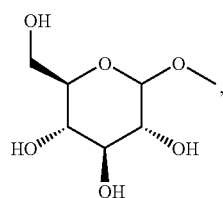

$R^2$ comprises moiety (iii) or (iv);
and
(e) when $R^1$ comprises —OCH$_2$CH$_2$OH, $R^2$ comprises moiety (iii).

16. The compound of claim 15, wherein said compound comprises 1-(2-hydroxyphenyl)-3-(pyridin-4-yl)propan-1-one.

17. An orally-receivable product comprising ancillary product compounds and at least one flavor providing compound, including salts thereof, of the formula:

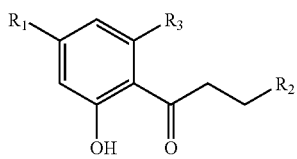

wherein $R^1$ comprises H, OH, O(CH$_2$)$_2$OH, OCH$_2$OCH$_3$ or

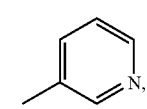

wherein $R^2$ comprises a heterocyclic moiety selected from:

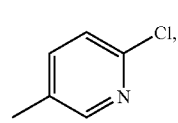 (i)

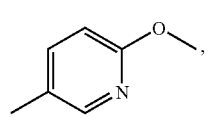 (ii)

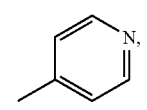 (iii)

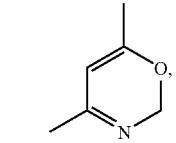 (iv)

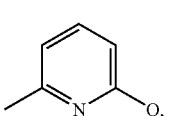 (v)

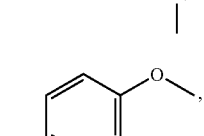 (vi)

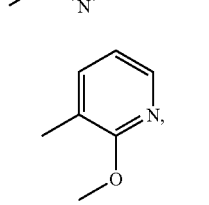 (vii)

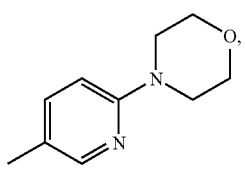 (viii)

(ix)

-continued

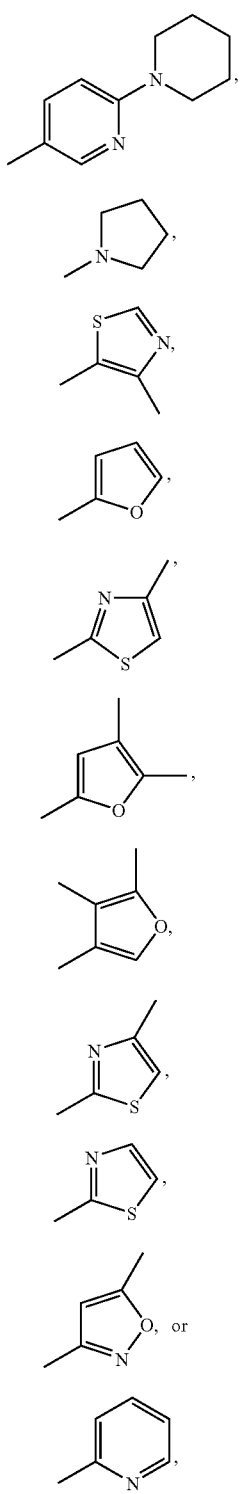

and wherein R₃ comprises H or OH.

18. The orally-receivable product of claim 17, wherein the product is selected from the group consisting of food products, food additives, nutraceuticals, pharmaceuticals, medicaments, beverages, beverage forms requiring reconstitution, tobacco products, chewing gum, oral care products, oral hygiene products, and combinations thereof.

19. The orally-receivable product of claim 17, wherein said flavor-providing compound comprises 1-(2-hydroxyphenyl)-3-(pyridin-4-yl)propan-1-one.

20. The orally-receivable product of claim 17, wherein said flavor-providing compound comprises 1-(2-hydroxyphenyl)-3-(pyridin-4-yl)propan-1-one and at least one other sweetness-enhancing compound.

21. A sweetener-containing consumable product comprising:
 a sweetener, ancillary product compounds, and
 at least one flavor providing compound, including salts thereof, of the formula:

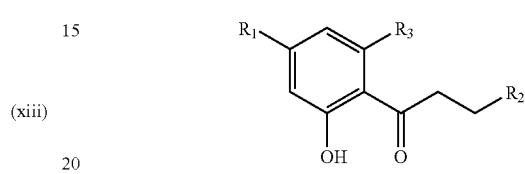

wherein $R^1$ comprises H, OH, O(CH₂)₂OH, OCH₂OCH₃ or

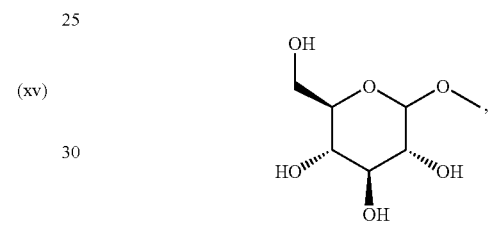

wherein $R^2$ comprises a heterocyclic moiety selected from:

(i)
(ii)
(iii)
(iv)
(v)
(vi)

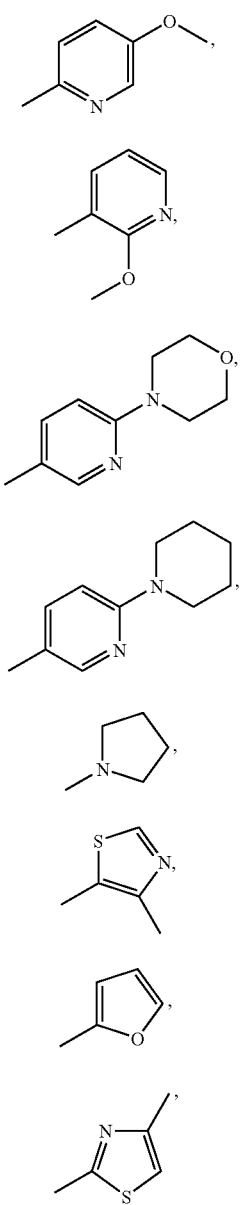
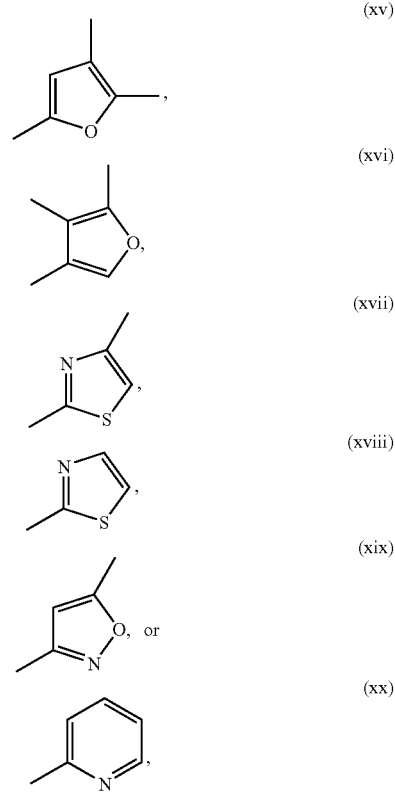

and wherein R₃ comprises H or OH.

22. The sweetener-containing consumable product of claim 21, wherein the product is selected from the group consisting of food products, food additives, nutraceuticals, pharmaceuticals, medicaments, beverages, beverage forms requiring reconstitution, tobacco products, chewing gum, oral care products, oral hygiene products, and combinations thereof.

23. The sweetener-containing consumable product of claim 21, wherein said flavor-providing compound comprises 1-(2-hydroxyphenyl)-3-(pyridin-4-yl)propan-1-one.

24. The sweetener-containing consumable product of claim 21, wherein said flavor providing compound comprises 1-(2-hydroxyphenyl)-3-(pyridin-4-yl)propan-1-one and at least one other sweetness-enhancing compound.

* * * * *